United States Patent
Umebayashi

(10) Patent No.: US 9,532,909 B2
(45) Date of Patent: Jan. 3, 2017

(54) DISPOSABLE WORN ARTICLE AND METHOD FOR MANUFACTURING SAME

(71) Applicant: Toyoshi Umebayashi, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 14 days.

(21) Appl. No.: 14/416,770

(22) PCT Filed: Jul. 25, 2013

(86) PCT No.: PCT/JP2013/070178
§ 371 (c)(1),
(2) Date: Jan. 23, 2015

(87) PCT Pub. No.: WO2014/021188
PCT Pub. Date: Feb. 6, 2014

(65) Prior Publication Data
US 2015/0173980 A1 Jun. 25, 2015

(30) Foreign Application Priority Data

Aug. 1, 2012 (JP) ................. 2012-171245

(51) Int. Cl.
*A61F 13/15* (2006.01)
*A61F 13/532* (2006.01)
(Continued)

(52) U.S. Cl.
CPC ..... *A61F 13/5323* (2013.01); *A61F 13/15634* (2013.01); *A61F 13/15658* (2013.01);
(Continued)

(58) Field of Classification Search
CPC ............. A61F 13/15634; A61F 13/15658; A61F 13/15699; A61F 13/15707; A61F 13/15723; A61F 13/15731; A61F 13/5323; A61F 2013/53051; A61F 2013/530554
See application file for complete search history.

(56) References Cited

U.S. PATENT DOCUMENTS 5,411,497 A  5/1995 Tamzer et al.
8,785,715 B2* 7/2014 Wright .............. A61F 13/15723
                                                          604/378
(Continued)

FOREIGN PATENT DOCUMENTS

JP  09-504210 A  4/1997
JP  10-165432 A  6/1998
(Continued)

OTHER PUBLICATIONS

International Search report for corresponding International Application No. PCT/JP2013/070178 mailed Oct. 29, 2013.

*Primary Examiner* — Bradley Philips
(74) *Attorney, Agent, or Firm* — Renner, Otto, Boisselle & Sklar, LLP

(57) ABSTRACT

An article including: an absorbent body including two liquid-permeable non-woven fabric sheets bonded together at bonded portions in a predetermined pattern, and a plurality of granular particles placed therebetween separately in each of a plurality of placement areas partitioned from one another in the predetermined pattern; and a non-liquid-permeable back sheet placed on a non-skin-contact surface of the absorbent body, wherein: a liquid-permeable sheet is placed so as to cover an entire surface of the non-woven fabric sheet on a skin-contact surface side; and an easily-breakable portion capable of being broken when the granular particles absorb a bodily fluid to swell is formed in placement areas on at least one non-woven fabric sheet.

5 Claims, 5 Drawing Sheets

(51) Int. Cl.
     B32B 37/00   (2006.01)
     B29C 65/08   (2006.01)
     B29C 65/00   (2006.01)
     *A61F 13/53*     (2006.01)
     *B32B 37/02*     (2006.01)
     *B32B 37/14*     (2006.01)
     *B32B 38/00*     (2006.01)
     *B32B 37/24*     (2006.01)
     *B32B 38/04*     (2006.01)
     *B29L 31/48*     (2006.01)

(52) U.S. Cl.
     CPC .. A61F 13/15699 (2013.01); A61F 13/15707 (2013.01); A61F 13/15723 (2013.01); A61F 13/15731 (2013.01); B29C 65/08 (2013.01); B29C 65/086 (2013.01); B29C 66/1122 (2013.01); B29C 66/21 (2013.01); B29C 66/234 (2013.01); B29C 66/433 (2013.01); B29C 66/7294 (2013.01); B29C 66/73921 (2013.01); B29C 66/834 (2013.01); B29C 66/83415 (2013.01); B32B 37/0076 (2013.01); *A61F 2013/53051* (2013.01); *A61F 2013/530554* (2013.01); *B29C 66/436* (2013.01); *B29C 66/8322* (2013.01); *B29L 2031/4878* (2013.01); *B32B 37/02* (2013.01); *B32B 37/144* (2013.01); *B32B 37/24* (2013.01); *B32B 38/0004* (2013.01); *B32B 2038/047* (2013.01); *B32B 2310/028* (2013.01); *B32B 2555/02* (2013.01); *Y10T 156/10* (2015.01); *Y10T 156/1052* (2015.01)

(56) References Cited

U.S. PATENT DOCUMENTS

| | | | |
|---|---|---|---|
| 2006/0278335 | A1 | 12/2006 | Moriura et al. |
| 2010/0100065 | A1* | 4/2010 | Bianco ............... A61F 13/5323 604/367 |
| 2012/0316048 | A1 | 12/2012 | Oba |
| 2013/0284362 | A1 | 10/2013 | Tsujimoto et al. |
| 2015/0038929 | A1* | 2/2015 | Van Malderen .... A61F 13/5323 604/370 |

FOREIGN PATENT DOCUMENTS

| | | |
|---|---|---|
| JP | 2005-59579 A | 3/2005 |
| JP | 2011-177350 A | 9/2011 |
| JP | 2012-050549 A | 3/2012 |
| WO | WO 2012/108330 A1 | 8/2012 |

* cited by examiner

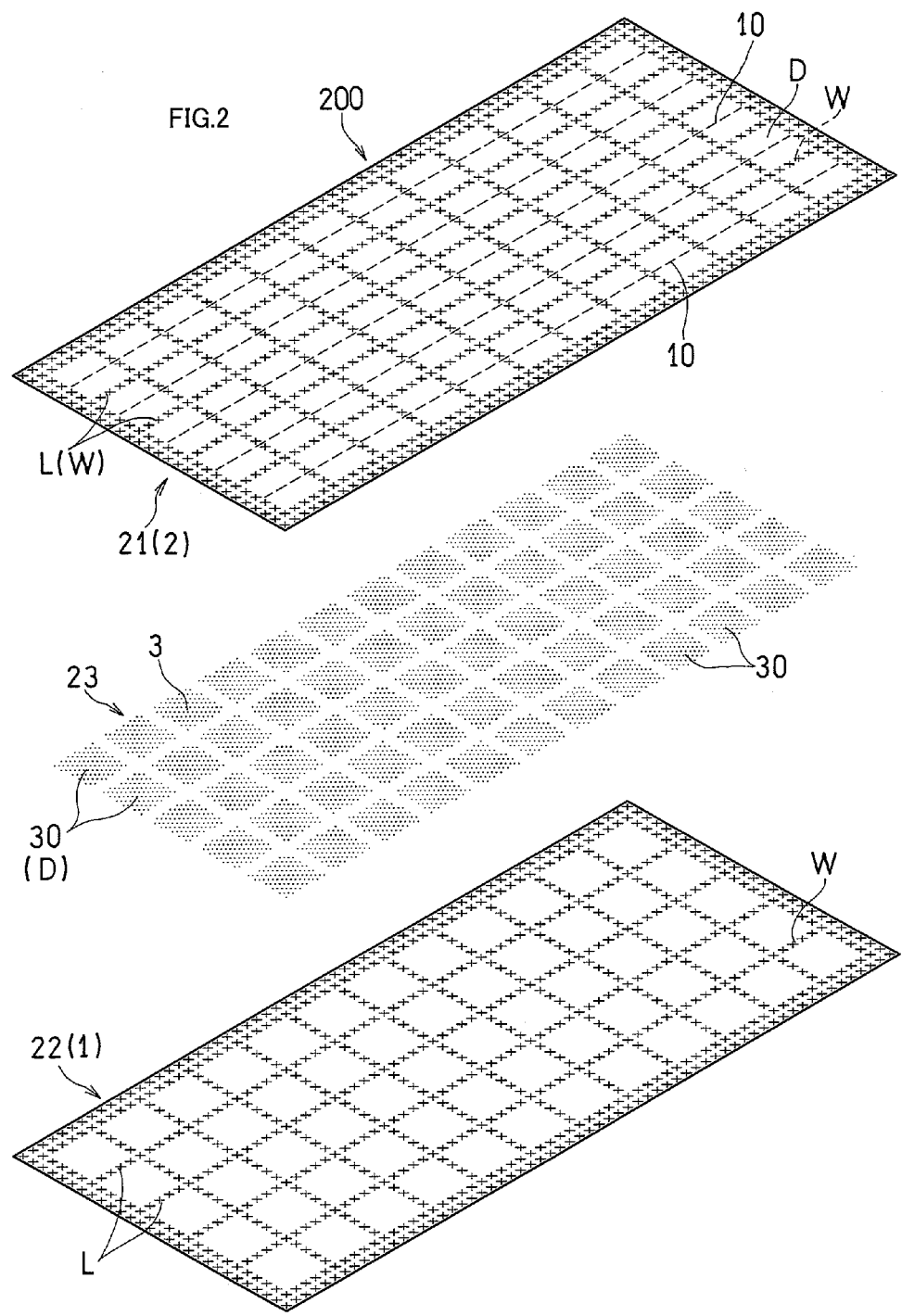

DISPOSABLE WORN ARTICLE AND METHOD FOR MANUFACTURING SAME

TECHNICAL FIELD

The present invention relates to a disposable worn article having a large number of granular particles (hereinafter referred to simply as "granular particles") capable of absorbing a bodily fluid to swell, and a method for manufacturing the same.

BACKGROUND ART

In recent years, absorbent cores have been proposed in the art, in which large amounts of granular particles are confined within a large number of small spaces (the first patent document). In an absorbent article of this type, granular particles are placed in a predetermined pattern between two base sheets, and the base sheets are bonded together along areas where the granular particles are absent.

The bonded portions between the base sheets are bonded with such a low strength that the base sheets are separated from each other by a separating force generated from swelling of a large number of granular particles within an area when the granular particles absorb moisture to swell. Then, the volume of granular particles that can be accommodated between two base sheets can be increased.

CITATION LIST

Patent Literature

[First Patent Document] JP09-504210 A

SUMMARY OF INVENTION

However, it is difficult to appropriately maintain the bonding strength of the portions that are bonded with a low strength.

As the bonded portions break due to swelling, the initial pattern of placement of granular particles loses its shape, thereby allowing the granular particles to be unevenly distributed between two base sheets.

It is therefore an object of the present invention to provide a disposable worn article with a simple structure capable of accommodating a large amount of granular particles, and a method for manufacturing the same.

The present invention is directed to a disposable worn article including:

an absorbent body including two liquid-permeable non-woven fabric sheets bonded together at bonded portions in a predetermined pattern, and a plurality of granular particles capable of absorbing a bodily fluid and then swelling, the granular particles placed between the two liquid-permeable non-woven fabric sheets and separately in each of a plurality of placement areas partitioned from one another in the predetermined pattern; and a non-liquid-permeable back sheet placed on a non-skin-contact surface of the absorbent body, wherein:

a liquid-permeable sheet is placed so as to cover an entire surface of one of the two non-woven fabric sheets that is on a skin-contact surface side; and an easily-breakable portion capable of being broken by a force that occurs when the granular particles absorb a bodily fluid and then swell is formed in at least one or more of the plurality of placement areas on at least one of the two non-woven fabric sheets.

In the present invention, as the granular particles absorb a bodily fluid to swell, the gap between the two non-woven fabric sheets greatly bulges, and as the granular particles further absorb a bodily fluid to swell, the easily-breakable portion formed in the placement area is broken by a force occurring upon swelling.

After the breakage, some granular particles are pushed out from the placement area of the absorbent body of two sheets through the broken easily-breakable portion. However, the non-skin-contact surface side of the absorbent body is covered by the back sheet, and the skin-contact surface side of the absorbent body is covered by another liquid-permeable sheet different from the non-woven fabric of the absorbent body. Therefore, a bodily fluid or granular particles having absorbed a bodily fluid will not leak out of the worn article.

The term "easily-breakable portion", as used in the present invention, refers to a portion which does not serve as an opening allowing granular particles to substantially seep out when the granular particles placed between the two non-woven fabric sheets have not swollen, but when the granular particles absorb a liquid to swell, the portion is broken by the force occurring in the placement area upon swelling, thereby allowing granular particles to seep out therethrough.

Thus, with a simple structure in which an easily-breakable portion is formed in at least one non-woven fabric sheet, it is possible to accommodate large amounts of granular particles in the placement areas.

Note that as used in the present invention, the term "skin-contact surface" refers to the inner surface to be in direct or indirect contact with the skin of the wearer when the worn article is worn, and the term "non-skin-contact surface" refers to the surface on the opposite side from the skin-contact surface.

BRIEF DESCRIPTION OF DRAWINGS

FIG. 2 is an exploded perspective view of an absorbent body of the worn article.

DESCRIPTION OF EMBODIMENTS

Figure 1A:
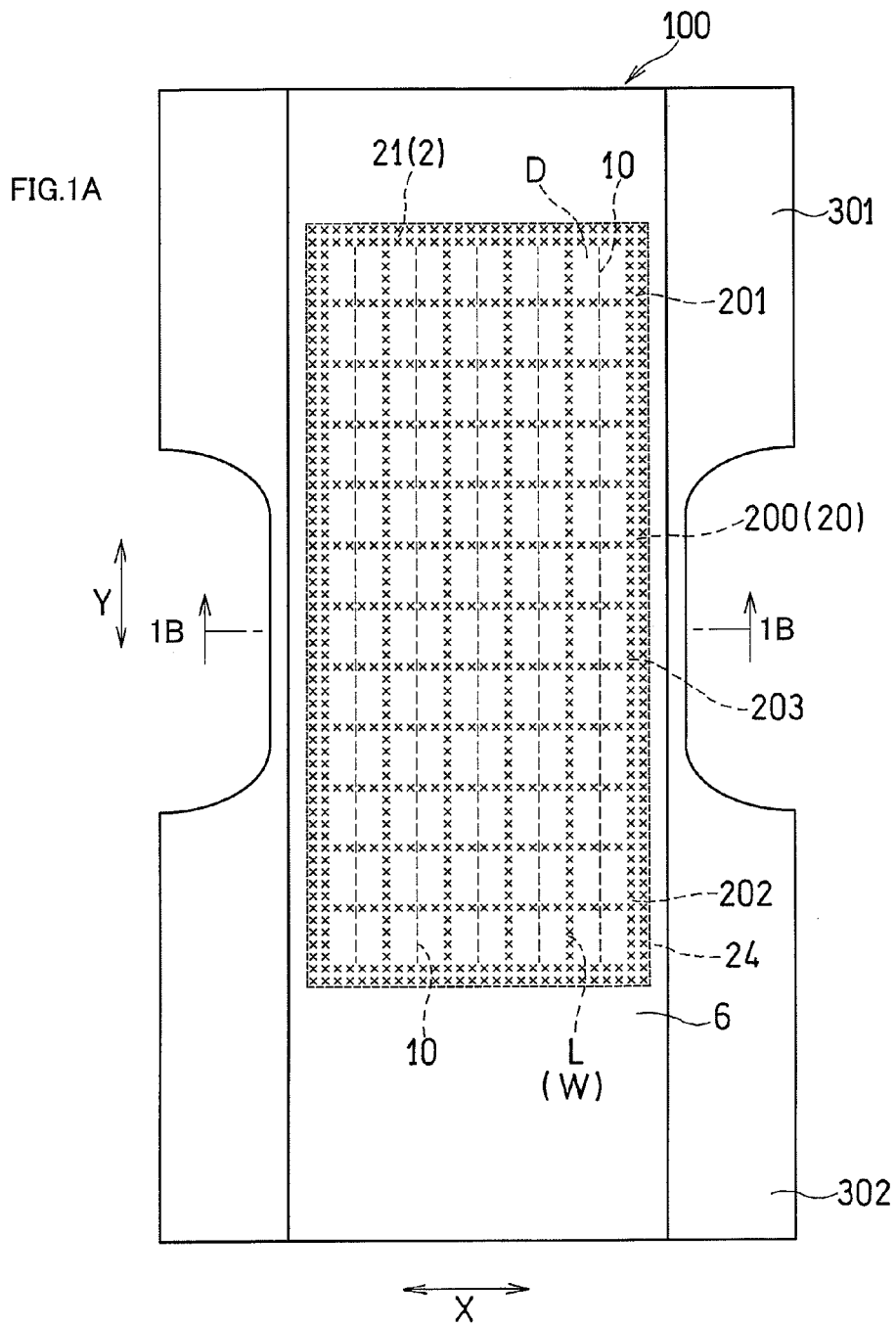
FIG. 1A is a plan view of a worn article according to an embodiment of the present invention.

Preferably, the bonded portions are ultrasonically-bonded portions formed by applying an ultrasonic energy to the two non-woven fabric sheets, and have a bonding strength such that the non-woven fabric sheets are not separated from each other at the bonded portions by a force that occurs when the granular particles absorb a bodily fluid to swell.

Where the non-woven fabric sheets are ultrasonically bonded together at bonded portions so that they are not separated from each other, if the granular particles absorb a bodily fluid to swell, the bonded portions will not break, but rather, the easily-breakable portion will break.

More preferably the easily-breakable portion is formed linearly and intermittently on the non-woven fabric sheet or sheets. That is, the easily-breakable portion is perforation-like.

When the non-woven fabric sheet having the easily-breakable portion is broken by the pressure of the granular particles swollen inside the absorbent body, such perforation-like easily-breakable portions connect together into a large opening. Thus, the granular particles can easily move out of the absorbent body through the easily-breakable portion. On the other hand, the non-woven fabric sheets, ultrasonically welded, are not separated from each other, thus making it unlikely that the initial pattern of placement of the granular particles loses its shape.

More preferably, the perforation-like easily-breakable portion includes a plurality of holes, slits and/or cuts (fissure) formed intermittently on the non-woven fabric sheet or sheets.

In such a case, when the granular particles absorb a liquid to swell, the perforation-like holes, slits or cuts are likely to connect together into a large opening.

In the present invention, a perforation-like "cut" forming an easily-breakable portion is not substantially open when no load is acting upon the non-woven fabric sheet, and it is therefore unlikely that granular particles move out of the absorbent body through the "cut" during manufacture or before use.

A "cut" refers to a line, along which the continuity of fibers is broken, produced in a non-woven fabric sheet without producing trimming chips.

Other than "cuts", the easily-breakable portion may be small apertures, thin rectangular slits, or diamond-shaped slits.

Alternatively, the easily-breakable portion may be a portion where the non-woven fabric sheet is hardened by heat so as to be brittle, thereby deteriorating (lowering) the strength.

Alternatively, the easily-breakable portion may be provided by forming the non-woven fabric sheet itself using a material that is more likely to be torn when pulled in the width direction.

Easily-breakable portions may be provided evenly among the placement areas or may be provided unevenly depending on the amount of granular particles in each placement area or depending on the position thereof in the absorbent body. Moreover, the easily-breakable portion may be absent for some placement areas where the amount of liquid to be absorbed is small.

A method for manufacturing the worn article set forth above includes the steps of:

carrying a carrier web, which is to form one of the two non-woven fabric sheets, along a predetermined carrying path while holding a first surface of the carrier web on a carrying surface of a carrying device;

dispensing the granular particles onto a second surface, opposite to the first surface, of the carrier web being carried;

placing the dispensed granular particles in the predetermined pattern by holding some of the dispensed granular particles in each of the placement areas on the second surface of the carrier web;

forming the easily-breakable portion on a cover web, which is to form the other one of the two non-woven fabric sheets;

after the step of placing the granular particles in the predetermined pattern, covering the second surface of the carrier web and the granular particles by the cover web having the easily-breakable portion therein, thereby producing a sandwich structure; and bonding together the carrier web and the cover web at positions to be the bonded portions so as to suppress or prevent the granular particles in the placement areas arranged in the predetermined pattern from moving from one of the plurality of placement areas into another placement area.

As the easily-breakable portion is formed in the non-woven fabric sheet before forming the sandwich structure, as described above, it is easy to form the easily-breakable portion.

Preferably, in the step of forming the easily-breakable portion, the easily-breakable portion is linearly formed intermittently or continuously along a flow direction of the carrier web and the cover web bonded together.

In such a case, even though there is a predetermined tension in the flow direction of the carrier web and the cover web as they are being carried, the easily-breakable portion, extending along the flow direction, is not widened open by the tension. Therefore, granular particles will not leak out through the easily-breakable portion while the sandwich structure is carried.

Embodiments

The present invention will be understood more clearly from the description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

One embodiment of the present invention will now be described with reference to the drawings.

Worn Article 100:

As shown in FIG. 1A, the worn article 100 of the present embodiment includes an absorbent body (diaper body) 200, a front around-torso member 301, and a back around-torso member 302. The absorbent body 200 includes a front portion 201 covering a front torso of the wearer, a back portion 202 covering the back torso of the wearer, and a crotch portion 203 covering the crotch between the front portion 201 and the back portion 202.

The crotch portion 203 is continuous with the front portion 201 and the back portion 202, and extends in the longitudinal direction Y perpendicular to the girth direction X. The front around-torso member 301 and the back around-torso member 302 may be bonded together when worn, or may be pre-bonded before being worn.

The absorbent body 200 may be provided with three-dimensional gathers (not shown).

The absorbent body 200 may include around-leg portions narrowed in conformity with the legs of the wearer.

Moreover, portions of the absorbent body 200 to be the around-leg portions may be provided with elastic members for fitting the worn article 100 to the wearer. The elastic members may be, for example, a plurality of rubber threads, rubber tapes, a film, a material including a thermoplastic resin, or the like. These materials may be provided in the front portion 201 and the back portion 202, and/or in the front around-torso member 301 and the back around-torso member 302, as elastic members for fitting the worn article 100 to the wearer.

As shown in FIG. 2, the absorbent body 200 includes a first web 21 to be in contact with the skin surface of the wearer, a second web 22 to be not in contact with the skin surface, and an absorbent core 23. The core 23 is sandwiched between the first web 21 and the second web 22.

Figure 3A:
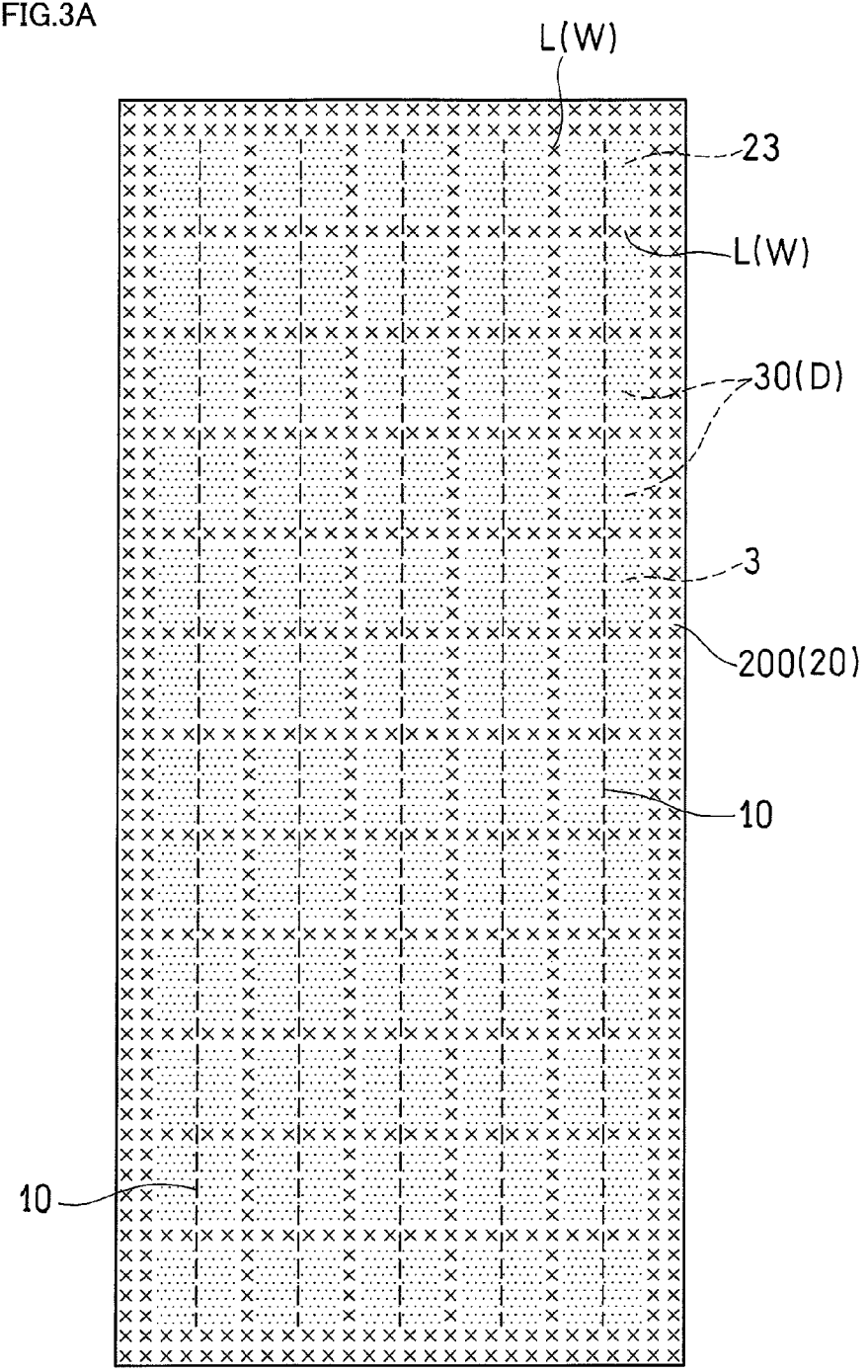
FIG. 3A is a plan view of the absorbent body.
Figure 3B:
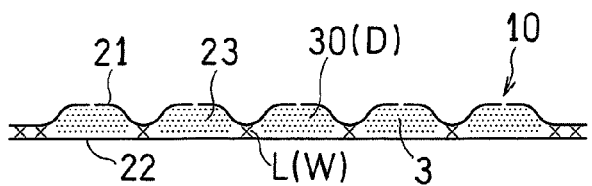
FIG. 3B is a cross-sectional view thereof.

The first web 21 and the second web 22 of FIG. 3B are welded together along lattice-shaped welded lines L, L extending in the length and width directions, for example, as shown in FIG. 3A, thereby forming a sandwich structure in which the core 23 is sandwiched therebetween. That is, as shown in FIG. 3B, the core 23 is surrounded by the first web 21 and the second web 22 welded together along the welded lines L, L.

Each welded line L is formed by bonded portions W along which the first web 21 and the second web 22 are welded together continuously or intermittently. The bonded portion W may be an ultrasonically-bonded portion formed by applying an ultrasonic energy to the two non-woven fabric sheets 21 and 22. The bonded portion W may have a bonding strength such that the non-woven fabric sheets 21 and 22 are not separated from each other at the bonded portion W by a force that occurs when the granular particles 3 absorb a bodily fluid and then swell.

Note that the welded bonded portions W are denoted by 'xx' in different figures.

Figure 1B:
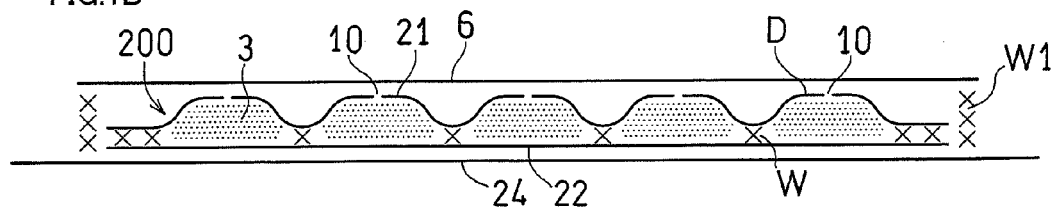
FIG. 1B is a cross-sectional view of the worn article taken along line 1B-1B.

The first web 21 and the second web 22 of FIG. 3B contain a thermoplastic resin such that they can be welded together, and are each formed by a non-woven fabric sheet that is liquid-permeable and air-permeable. In FIG. 1B, a non-liquid-permeable back sheet 24 is attached to the non-skin-contact surface of the second web 22, and the absorbent article 200 is covered by the back sheet 24. On the other hand, a liquid-permeable top sheet 6 covering the entire surface of the first web 21 is placed on the skin-contact surface of the first web 21.

Note that the non-woven fabric sheet may be a thermoplastic resin non-woven fabric sheet such as polypropylene, polyethylene, polyester, or the like, and it may also be a non-woven fabric sheet obtained by blending together non-thermoplastic fibers such as cotton or rayon with the thermoplastic resin fibers.

The core 23 includes a large number of absorbent granular particles 3. The granular particles 3 are made of a well-known absorbent high-molecular polymer whose average granular diameter is typically about 10 μm to about 1,000 μm before absorbing moisture and which swell after absorbing moisture to a volume several times to several hundreds of times larger.

Note that the granular particles 3 are denoted by a larger number of minute dots in different figures. The granular particles 3 are not shown in FIGS. 1A and 5A to 5C so as to make easily-breakable portions 10 more visible.

The core 23 of FIG. 3A includes aggregate groups 30 placed in a large number of placement areas D, the aggregate groups 30 each having an aggregate of a large number of granular particles 3. The aggregate groups 30, 30 are separately arranged in the placement areas D, D partitioned by lattice-shaped welded lines L, L extending in the length and width directions. That is, the placement areas D, D, in which the aggregate groups 30, 30 are placed, are partitioned from one another by the welded lines L, L.

In other words, each aggregate group 30 is composed of an aggregate of a large number of granular particles 3, and the aggregate groups 30 are arranged in the length and width directions with welded lines L, L therebetween, as shown in FIG. 3A. As shown in FIG. 3A, a larger number (three or more) of aggregate groups are arranged in the length and width directions.

A welded line L does not need to be completely continuous, and may be an intermittent array of welded positions such that the granular particles 3 in one aggregate group 30 cannot easily move into other aggregate groups 30.

That is, the welded lines L, L may be formed to such a degree that it is possible to suppress the movement of granular particles 3 from one of the aggregate groups 30, arranged in a predetermined pattern, into another.

The arrangement of the aggregate groups 30 may be any predetermined pattern, and does not need to be a regular array extending in the length and width directions. The number (volume) of granular particles 3 contained in each aggregate group 30 does not need to be generally equal to that in other groups, and the number (volume) of each aggregate group 30 may be determined based on the amount of bodily fluid to be discharged.

As shown in FIG. 3A, the aggregate groups 30 may be rectangular or circular, and the length of each side or the diameter thereof may be some millimeters to about 10 millimeters. The pitch at which the aggregate groups 30, 30 are placed may be about 10 mm to about ten-odd mm.

Next, an important part of the present invention will be described.

As shown in FIGS. 1A to 2, each placement area D of the first web 21 includes a perforation-like easily-breakable portion 10 including intermittent "cuts", for example.

The easily-breakable portion 10 may be provided on at least one of the two non-woven fabric sheets 21 and 22, and it breaks by a force that occurs when the granular particles 3 absorb a bodily fluid to swell. That is, in the present embodiment, when the easily-breakable portion 10 of the first web 21 breaks, the intermittent "cuts" connect together into a long "cut", thereby allowing a bodily fluid or the granular particles 3 having absorbed a bodily fluid to seep (spill) out from between the two webs 21 and 22 onto the upper surface of the first web 21.

Therefore, before being used, large amounts of granular particles 3 can be accommodated in the placement areas D. On the other hand, the top sheet 6 covering the entire surface of the first web 21 is provided on the skin-contact surface side of the first web 21 so that the swollen granular particles 3 overflowing through the cut will not contact the skin of the wearer of the worn article 100.

Note that between the top sheet 6 and the first web 21, there may be a diffusing layer for diffusing a bodily fluid in the surface direction (along the surface) of the core 23, or a liquid-holding layer for temporarily holding a bodily fluid.

Next, an outline of a method for manufacturing a sandwich structure 20 will be described.

Figure 4:
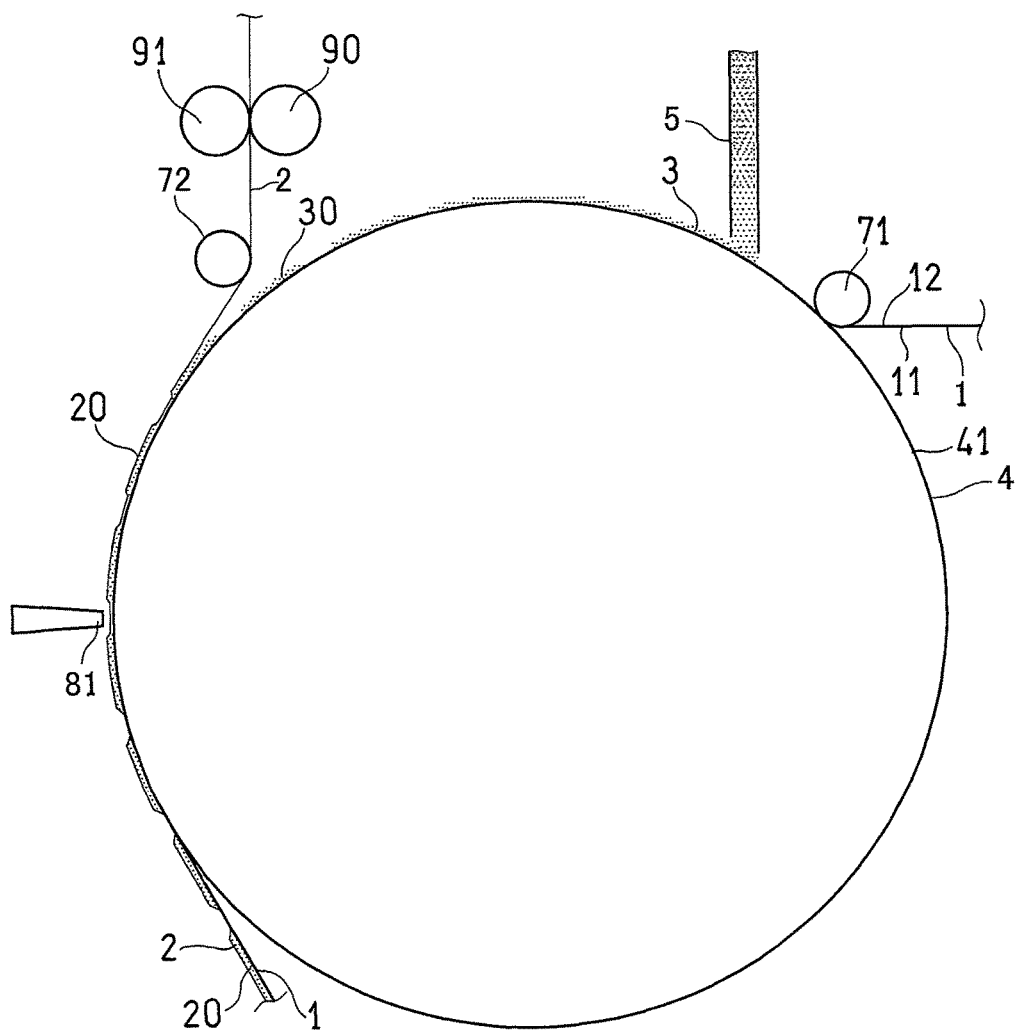
FIG. 4 is a schematic side view of a device for manufacturing the absorbent body.

As shown in FIG. 4, a carrier web 1 to be the second web 22 (FIG. 2) is introduced onto a carrying drum 4 by a first introduction roller 71, and the carrier web 1 is carried along a predetermined carrying path, i.e., along the carrying surface 41 of the carrying drum 4, while a carrying surface 41 of the carrying drum 4 holds by suction a first surface 11 of the carrier web 1.

Between the first introduction roller 71 and a second introduction roller 72, a dispenser device 5 dispenses a large number of granular particles 3 onto a second surface 12, opposite to the first surface 11, of the carrier web 1 being carried. The dispensed granular particles 3 form a layer on the second surface 12.

As an air is drawn toward suction holes (not shown) formed on the carrying drum 4, the dispensed granular particles 3 are held by suction, in aggregate groups 30, in the placement areas D of the second surface 12 on the carrier web 1.

Note that an airflow deflector may be provided opposing the second surface 12 of the carrier web 1, the airflow deflector giving at least a part of the air a flow component flowing in a direction along the second surface 12 of the carrier web 1. (PCT/JP2012/52371)

The granular particles 3 may be dispensed intermittently for each absorbent body 200 (FIG. 1).

The layer of granular particles 3 may have a greater thickness in its center than in its opposite end portions in the axial direction of the carrying drum 4. Alternatively, the layer of granular particles 3 may have a smaller thickness along the periphery of one absorbent body 200 (FIG. 1) and have a greater thickness in the center of the layer and/or the vicinity of the center.

On the other hand, the easily-breakable portions 10 (FIG. 2) are formed on a cover web 2 to be the first web 21 (FIG. 2) in advance before the cover web 2 is introduced onto the carrying drum 4. That is, perforation-like cuts are formed in the cover web 2 between a cutter roll 90 and an anvil roll 91, which are placed upstream of the second introduction roller 72.

As shown in FIG. 3A, after the granular particles 3 dispensed from the dispenser device 5 are placed in a predetermined pattern (separately in the placement areas D) on the carrier web 1, the second surface 12 (FIG. 4) of the carrier web 1 where the granular particles 3 are absent, and the granular particles 3 placed on the carrier web 1 are covered by the cover web introduced by the second introduction roller 72, thereby producing the sandwich structure 20.

Then, as the sandwich structure 20 continues to be carried by the carrying surface 41 to reach an ultrasonic horn 81 of FIG. 4, the carrier web 1 and the cover web 2 are ultrasonically welded together at positions where the granular particles 3 are absent (FIG. 2). Thus, the aggregate groups 30 of the granular particles 3 are partitioned from one another by the carrier web 1 and the cover web 2, ultrasonically welded together, thereby maintaining a predetermined pattern of the granular particles 3.

That is, the carrier web 1 and the cover web 2 are bonded together at positions to be the bonded portions W so as to suppress or prevent the granular particles 3 (the aggregate groups 30) in the placement areas D arranged in the predetermined pattern from moving from one of the plurality of placement areas D into another placement area D.

Then, the sandwich structure 20 is cut into individual worn articles, i.e., into individual absorbent bodies 200 shown in FIG. 3A.

Figure 5A:
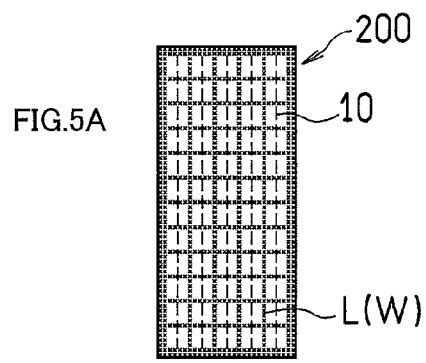
FIGS. 5A, 5B and 5C are plan views each showing a method for manufacturing the worn article.
Figure 5B:
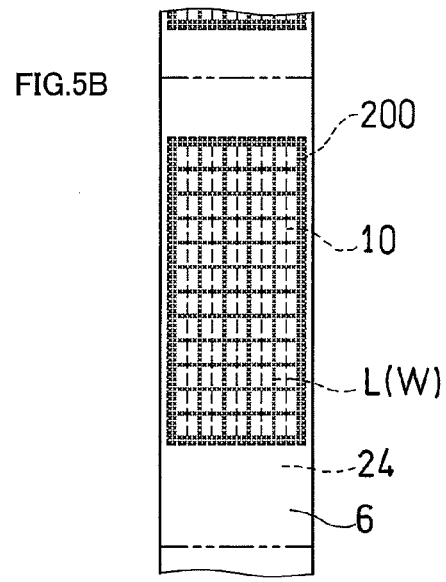
Figure 5C:
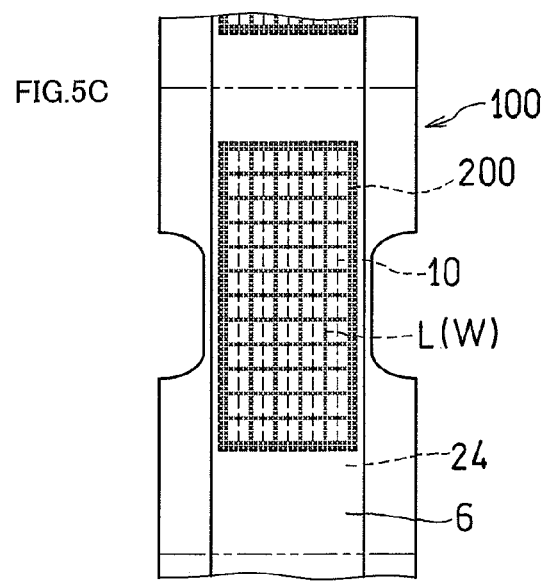

Then, as shown in FIGS. 5A to 5C, each absorbent body 200 is sandwiched between the liquid-permeable top sheet 6 and the non-liquid-permeable back sheet 24. Note that the top sheet 6 and the back sheet 24 may be bonded or welded together along a peripheral bonded portion W1 (FIG. 1B). The back sheet 24 and the absorbent body 200 may also be bonded together.

Next, how the present article is used will be described.

As a bodily fluid is absorbed by the absorbent body 200 including the first web 21 having the easily-breakable portion 10 of FIG. 1A and the top sheet 6 covering the first web 21, the granular particles 3 of FIG. 1B swell with the bodily fluid, thereby expanding the gap between the first web 21 (non-woven fabric sheet) and the second web 22 (non-woven fabric sheet). As the load applied on the first web 21 becomes excessive due to the swelling of the granular particles 3, the first web 21 is ripped along the easily-breakable portion 10 of FIG. 1A, and the cuts of the easily-breakable portion 10 of the first web 21 connect together, thereby breaking a portion of the first web 21 in the placement area D.

On the other hand, the first web 21 and the second web 22, which are ultrasonically welded at the bonded portions W are not separated from each other by the swelling of the granular particles 3.

Although a bodily fluid or the granular particles 3 having absorbed a bodily fluid overflows through the ripped easily-breakable portions 10 of the first web 21, the top sheet 6 of FIG. 1B covers the upper surface of the absorbent body 200, preventing the swollen granular particles 3 or the bodily fluid from contacting the skin of the wearer of the worn article 100 of FIG. 1A to deteriorate the wearability.

While preferred embodiments have been described above with reference to the drawings, obvious variations and modifications will readily occur to those skilled in the art upon reading the present specification.

For example, a conveyer, rather than a drum, may be employed as the carrying device.

The method for bonding the carrier web 1 and the cover web 2 with each other may be thermal welding such as heat seal or may be adhesion using an adhesive, for example, instead of ultrasonic welding.

The present invention is not limited to cases where each placement area D includes therein only an aggregate of granular particles, and each placement area D may include therein a plurality of granular particles mixed with another granular material or a fiber material such as a pulp.

Thus, such changes and modifications are deemed to fall within the scope of the present invention, which is defined by the appended claims.

INDUSTRIAL APPLICABILITY

The present invention is applicable to disposable worn articles including granular particles placed in a predetermined pattern, as well as absorbent bodies.

REFERENCE SIGNS LIST

1: Carrier web (non-woven fabric sheet), 10: Easily-breakable portion, 11: First surface, 12: Second surface
2: Cover web (non-woven fabric sheet), 20: Sandwich structure, 21: First web, 22: Second web, 23: Core, 24: Back sheet
3: Granular particles, 30: Aggregate group, D: Placement area
4: Carrying drum, 41: Carrying surface
5: Dispenser device
6: Top sheet
71: First introduction roller, 72: Second introduction roller
81: Ultrasonic horn
100: Worn article, 200: Absorbent body (diaper body), 201: Front portion, 202: Back portion, 203: Crotch portion, 301: Front around-torso member, 302: Back around-torso member
L: Welding line
X: Girth direction, Y: Longitudinal direction
W: Bonded portion
W1: Bonded portion

The invention claimed is:
1. A disposable worn article comprising:
an absorbent body including two liquid-permeable non-woven fabric sheets bonded together at bonded portions in a predetermined pattern, and a plurality of liquid-absorbing granular particles, the granular particles placed between the two liquid-permeable non-woven fabric sheets and separately in each placement area of a plurality of placement areas partitioned from one another by the predetermined pattern, wherein the each placement area is one area that is surrounded by the bonded portions and excludes the bonded portions, the bonded portions are ultrasonically-bonded portions formed by applying an ultrasonic energy to the two non-woven fabric sheets, and have a bonding strength such that the non-woven fabric sheets are not separated from each other at the bonded portions by a force that occurs when the granular particles absorb a bodily fluid to swell; and a non-liquid-permeable back sheet placed on a non-skin-contact surface of the absorbent body, wherein:

a liquid-permeable sheet is placed so as to cover an entire surface of one of the two non-woven fabric sheets that is on a skin-contact surface side;

an easily-breakable portion capable of being broken by a force that occurs when the granular particles absorb a bodily fluid to swell is formed linearly and intermittently in at least one or more of the plurality of placement areas on at least one of the two non-woven fabric sheets; and the easily-breakable portion is linearly formed by including a plurality of holes, slits and/or cuts formed intermittently on the at least one of the non-woven fabric sheets in each of the at least one or more of the plurality of placement areas.

2. A method for manufacturing an article according to claim 1, comprising the steps of:

carrying a carrier web, which is to form one of the two non-woven fabric sheets, along a predetermined carrying path while holding a first surface of the carrier web on a carrying surface of a carrying device;

dispensing the granular particles onto a second surface, opposite to the first surface, of the carrier web being carried;

placing the dispensed granular particles in the predetermined pattern by holding some of the dispensed granular particles in each of the placement areas on the second surface of the carrier web;

forming the easily-breakable portion on a cover web, which is to form the other one of the two non-woven fabric sheets;

after the step of placing the granular particles in the predetermined pattern, covering the second surface of the carrier web and the granular particles by the cover web having the easily-breakable portion therein, thereby producing a sandwich structure; and bonding together the carrier web and the cover web at positions to be the bonded portions so as to suppress or prevent the granular particles in the placement areas arranged in the predetermined pattern from moving from one of the plurality of placement areas into another one of the placement areas.

3. A method according to claim 2, further comprising the steps of:

cutting the sandwich structure into each absorbent body;

sandwiching the each absorbent body between the liquid-permeable sheet and the back sheet.

4. A method according to claim 3, wherein in the step of forming the easily-breakable portion, the easily-breakable portion is linearly formed intermittently or continuously along a flow direction of the carrier web and the cover web bonded together.

5. A worn article according to claim 1, wherein the bonded portions include a plurality of first portions extending in a first direction and a plurality of second portions extending in a second direction that crosses the first direction, and the first portions adjacent with one another and the second portions adjacent with one another partition the plurality of placement areas.

* * * * *